(12) United States Patent
Massaro et al.

(10) Patent No.: US 6,303,648 B1
(45) Date of Patent: Oct. 16, 2001

(54) METHODS AND COMPOSITIONS FOR THE TREATMENT AND PREVENTION OF LUNG DISEASE

(75) Inventors: Gloria DeCarlo Massaro; Donald Massaro, both of Washington, DC (US); Roshantha A. Chandraratna, Laguna Hills, CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/548,897

(22) Filed: Apr. 13, 2000

Related U.S. Application Data

(60) Provisional application No. 60/129,213, filed on Apr. 14, 1999.

(51) Int. Cl.$^7$ .......................... A61K 31/38; A61K 31/34; C07D 333/24; C07C 69/76; C07C 63/33
(52) U.S. Cl. .......................... 514/461; 514/438; 514/533; 514/568; 514/569; 549/79; 549/80; 560/61; 560/85; 562/405
(58) Field of Search .................. 549/80, 79; 514/461, 514/533, 568, 569, 438; 560/61, 85; 562/405

(56) References Cited

U.S. PATENT DOCUMENTS

| 5,728,846 | 3/1998 | Vuligonda et al. |
| 5,739,338 | 4/1998 | Beard et al. |
| 5,760,276 | 6/1998 | Beard et al. |
| 5,776,699 | * 7/1998 | Klein |
| 5,877,207 | 3/1999 | Klein et al. |

FOREIGN PATENT DOCUMENTS

| 0 747 347 | 7/1999 | (EP) |
| 93/11755 | 6/1993 | (WO) |

OTHER PUBLICATIONS

Sun, CA 128:43515, abstract, 1997.*
Klein, CA 126:277406, abstract, 1997.*
Johnson, CA 126:99161, abstract, 1996.*
Vuligonda, CA 125:195216, abstract, 1996.*

Massaro et al, "Retinoic acid treatment abrogates elastase–induced pulmonary emphysema in rats", Nature Medicine, vol. 3, No. 6,675–677 (1997).

Massaro et al, "Postnatal treatment with retinoic acid increases the number of pulmonary alveoli in rats", Am. J. Physiol., 270, L305–L310 (1996).

Nagpal et al, "Retinoids as Anti–Cancer Agents", Current Pharm. Design Jun; 2(3): 295–316 (1996).

Mangelsdorf et al, "The Retinoid Receptors, Biology", Chemistry and Medicine Ch. 8 (2d ed. Sporn et al eds. 1994), 319–349.

Burri et al, "The Postnatal Growth of the Rat Lung I. Morphometry", Anat. Rec.178: 711–730 (1973).

Burri et al, "The Postnatal Growth of the Rat Lung III. Morphology", Anat. Rec., 180: 77–98 (1974).

Massaro et al, "Formation of Pulmonary Alveoli and Gas––Exchange Surface Area: Quantitation and Regulation", Annu. Rev. Physiol, 58, 73–92, 1996.

Shapiro, "The Pathogenesis of Emphysema: the Elastase: Antielastase Hypothesis 30 Years Later", Proceedings of the Association of American Physicians, 107:3, 1995, 346–352.

Reczek et al, "Role of Retinoic Acid Receptor Gamma in the Rhino Mouse and Rabbit Irritation Models of Retinoid Activity", Skin Pharmacol 1995; 8: 292–299.

* cited by examiner

*Primary Examiner*—D. Margaret Seaman
(74) *Attorney, Agent, or Firm*—Carlos A. Fisher; Robert J. Baran; Martin A. Voet

(57) ABSTRACT

Methods and compositions for the treatment of lung disease, such as emphysema and/or bronchopulmonary dysplasia, in a mammal. Also disclosed are methods promoting the formation of alveolar septa and increasing the gas-exchange surface area of a mammalian lung, and for the prevention and/or treatment of alveolar destruction.

7 Claims, 2 Drawing Sheets

METHODS AND COMPOSITIONS FOR THE TREATMENT AND PREVENTION OF LUNG DISEASE

This application claims priority under 35 USC § 119(e) to Provisional Application No. 60/129,213, filed Apr. 14, 1999.

FIELD OF THE INVENTION

This invention concerns the use of retinoic acid receptor (RAR) antagonists for the inhibition of alveolar destruction and/or to promote the formation of alveoli in mammalian lung tissue deficient in adequate numbers of functional alveoli.

BACKGROUND OF THE INVENTION

Among aerobic animals, the lung functions to provide an interface for the exchange of gases between blood and the atmosphere. The agents of this exchange are numerous small sacs termed alveoli (in adult humans about 300,000,000 per lung) that provide a gas permeable-liquid impermeable barrier between the gas and liquid phases. Between the alveoli are numerous capillaries carrying deoxygenated blood to the lung from the tissues and oxygenated blood from the alveoli to the tissues. The partial pressure of oxygen in the lungs is approximately 100 mm Hg at sea level; at this pressure the binding of oxygen by hemoglobin in the erythrocytes is favored. The alveoli thus provide a means for presenting the oxygen to hemoglobin to permit the conversion of deoxyhemoglobin to hemoglobin. Because the exchange occurs at the surface of the gas/blood barrier, alveoli have evolved as a means for providing extremely high surface area in a compact overall area, thus maximizing possible gas exchange. Lack of adequate gas exchange would lead to disability which could progress to death.

Diseases that result in fewer alveoli therefore are quite serious, and are common causes of inadequate oxygenation and resultant disability and death. Among such diseases are brochopulmonary dysplasia (BPD) and emphysema. BPD is a disease of prematurely born infants, and is characterized mainly by a failure of the infant to form a sufficient number of appropriately-sized alveoli. Emphysema, a disease of middle and advanced age, appears to be due to progressive proteinase-induced alveolar destruction.

The process of alveoli formation is reasonably well understood from a gross developmental standpoint, and seems to be similar in rat, mouse, and human, the major species studied. The process includes the subdivision (septation) of the saccules that constitute the gas-exchange region of the immature lung. Septation results in the formation of smaller, more numerous gas-exchange structures (alveoli). The timing of the onset and cessation of septation vary among species, but both onset and cessation are critical to the formation of alveoli of the size and number needed for adequate oxygenation.

The molecular basis of the initiation and cessation of alveoli formation are not as well understood as the structural events and timing accompanying alveoli development. Knowledge of the molecular signals that initiate and end septation, and that govern the spacing of septa relative to the $O_2$-demand, are virtually unknown; however, several lines of evidence suggest that certain retinoids (retinoic acid and its derivatives) may play a key signaling role. In Massaro et al., *Nature Medicine* 3:675 (1997), hereby incorporated by reference herein, rats were treated with elastase, causing destruction of alveolar walls in a manner similar to that seen in pulmonary emphysema. Treatment of the rats with all-trans-retinoic acid (ATRA), an agonist of all RAR isotypes, appeared to reverse this destruction. Similarly, treatment of newborn rats (which are born with immature lungs lacking an adult complement of alveoli) with ATRA induced the formation of an increased number of alveoli in rats without enlarging the lung. See Massaro et al., *Am. J. Physiol.* 270: L305 (1996) incorporated by reference herein.

ATRA can have a multiplicity of physiological effects. The retinoid receptors, when bound by an appropriate ligand, are mediators of various life processes, including reproduction, metabolism, differentiation, hematopoiesis, and embryogenesis.

There is therefore a need for methods and compositions that provide a practicable means for inhibiting alveolar destruction and/or promoting the formation of alveoli in a postnatal aerobic animal, particularly a mammal such as a human. Additionally, there is a need for therapeutic methods that are able to more specifically treat such a condition without a high likelihood of serious side effects.

SUMMARY OF THE INVENTION

Figure 1A:
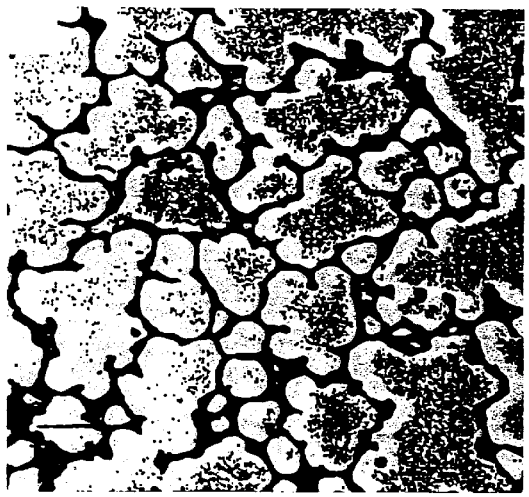
FIG. 1A is a photomicrograph of a histological section of the lung of a 14-day old rat injected intraperitoneally daily from age 3 to 13 days with cottonseed oil (control).

The present invention is directed to methods and compositions for promoting the formation of alveoli in mammalian lung tissue. In one embodiment the invention comprises a therapeutic method for inducing the formation of alveoli in mammalian lung tissue by administration of a composition comprising a therapeutically effective amount of an ligand that is an RARβ antagonist or inverse agonist. In a preferred aspect of this embodiment, the RARβ receptor antagonist or inverse agonist has specific RAR modulating activity at the RARβ receptor, and is not specific to the RARα receptor. In another preferred aspect, the RARβ receptor antagonist or inverse agonist has specific RAR modulating activity at the RARβ receptor and is not specific to the RARγ receptor. In a particularly preferred aspect of this embodiment, the RARβ receptor antagonist or inverse agonist has specific RAR modulating activity at the RARβ receptor and is not specific to either the RARα or the RARγ receptor. Even more preferably, the ligand is specific to RARβ isotypes. Preferably such a ligand is a retinoid.

By "specific RAR modulating activity" is meant that such a compound has a disassociation constant ($K_D$) (the ligand concentration at which 50% of the RAR receptors are complexed with the ligand) at an RAR receptor at least 10 times, preferably at least 25 times, even more preferably at least 50 times, and most preferably at least 100 times greater than the $K_D$ for the binding of the same ligand to an RXR receptor. Determination of the $K_D$ at an RAR or RXR receptor for a given ligand is a routine matter. Membrane preparations of host cells expressing a cloned RAR or RXR receptor, and the amino acid and nucleotide sequences of such receptors, has been described in various publications available, and within the knowledge of, the person or ordinary skill in the art. For example, U.S. Pat. No. 5,776, 699, to Klein et al., describes assays employing RAR and RXR, and PCT Publication No. WO93/11755 discloses ligand binding assays. These references are now incorporated by reference herein in their entirety.

By "agonist" is meant a retinoid receptor ligand that will cause the activation of transcription at a gene having an appropriate retinoid receptor response element.

By "antagonist" is meant a retinoid receptor ligand that will inhibit the activation of transcription by the retinoid receptor at a gene having an appropriate retinoid receptor response element in the presence of an agonist of the retinoid receptor.

By "inverse agonist" is meant a retinoid receptor ligand that will inhibit the expression of transcription at a gene having an appropriate retinoid receptor response element beyond a basal expression level existing in the absence of an agonist of the retinoid receptor.

In another embodiment, the invention is directed to therapeutic compositions for the treatment of an emphysemic mammal, or of a mammal suffering from bronchopulmonary dysplasia, comprising a therapeutically effective amount of an ligand that is an RARβ antagonist or inverse agonist. In a preferred aspect of this embodiment, the RARβ receptor antagonist or inverse agonist has specific RAR modulating activity at the RARβ receptor, and is not specific to the RARα receptor. In another preferred aspect, the RARβ receptor antagonist or inverse agonist has specific RAR modulating activity at the RARβ receptor and is not specific to the RARγ receptor. In a particularly preferred aspect of this embodiment, the RARβ receptor antagonist or inverse agonist has specific RAR modulating activity at the RARβ receptor and is not specific to either the RARα or the RARβ receptor. Even more preferably, the ligand is specific to RARβ isotypes. Preferably such a ligand is a retinoid. It is contemplated that the RARβ antagonist or inverse agonist may be used either as the only active ingredient in the composition, or in combination with one or more additional therapeutically active ingredient. In one aspect, the additional therapeutically active ingredient is a retinoid; in a preferred aspect, an additional therapeutically active ingredient is another RAR-active ligand, for example, all-trans-retinoic acid.

By "RAR-active retinoido" is meant that the retinoid has agonist, inhibitory, or inverse agonist (negative hormone) activity at an RAR receptor.

By "therapeutically effective amount" is meant that the amount of the RAR-specific therapeutic agent is sufficient, either as the result of a single dose, or as the result of multiple doses over the term of therapy, to decrease the rate of alveolar destruction in an emphysemic mammal, or to promote the growth of alveolar septa in said mammal.

DETAILED DESCRIPTION OF THE DRAWINGS

The present invention is directed to compositions and methods for the treatment or prevention of alveolar destruction and/or to promote the formation of alveoli is mammalian lungs deficient in adequate numbers of functional alveoli. Such methods and compositions involve RAR-active retinoids, therapeutic compositions containing such agents, and methods for their use.

The retinoid receptors are part of the steriod/thyroid/vitamin D superfamily of nuclear receptors. The retinoid receptors include the retinoic acid receptors (RAR) and the retinoid X receptor (RXR). The RAR and RXR receptors are single chain polypeptides containing a number of structural domains in common: a ligand binding domain, a sequence-specific DNA binding domain, and a leucine zipper motif. In the presence of ligand, the single RAR or RXR chains can, by virtue of the leucine zipper, form dimers. The RAR chain is believed to exist in vivo exclusively as an RAR/RXR heterodimer. RXR may form heterodimers with RAR or other members of the superfamily, such as the vitamin D receptor and the thyroid receptor.

Retinoid receptor dimers are effective transcription factors regulating gene transcription by binding to retinoic acid response elements (RAREs) or retinoid X response elements (RXREs) present in (or near) the promoters of retinoid responsive genes, or by negatively regulating the enhancer functions of other transcription factors.

Described RAR isotypes include RARβ, RARα, and RARγ, and described RXR isotypes include RARβ, RARα, and RARγ. Within each receptor class, these isotypes have sequence homology, but are encoded by different genes. Within each isotype several isoforms have been described; these isoforms differ in their N terminals and are generated by alternative splicing and/or differential usage of more than one promoter. See e.g., Nagpal & Chandraratna, *Current Pharm. Design* 2:295–316 (1996) and Mangelsdorf et al., *The Retinoid Receptors* in *The Retinoids: Biology, Chemistry and Medicine* Ch. 8(2d ed. Sporn et al. eds. 1994), both of which are hereby incorporated by reference herein.

Depending both upon the ligand and the nature (e.g., RAR or RXR; isotype; isoform) of the monomer chains contained in the dimers, an enormous variety of biological responses regulated by the retinoid receptors are possible.

Ligands specific to RAR (e.g., ATRA) or RXR (e.g., TTNB), and to specific RAR isotypes have been described. See e.g., Nagpal & Chandraratna, *Current Pharm. Design* 2:295–316 (1996). Therefore, the design and/or selection of RAR-specific ligands, and of RAR isotype-specific ligands is well within the ability of the person of ordinary skill in the art.

By "specific" to a given retinoid receptor is meant that the disassociation constant ($K_D$) for the binding of the ligand to a given target receptor or receptor isotype or isoform is at least 10 times lower than the $K_D$ value for the ligand and a non-target receptor or receptor isotype or isoform. $K_D$ is defined as the concentration of ligand at which 50% of the receptors are ligand bound. Even more preferably, $K_D$ is at least 25 times lower for the target receptor than for untargeted receptors. Most preferably, $K_D$ is at least 50, or at least 100, times lower for the target receptor than for untargeted receptors.

An aspect of the present invention comprises compositions for the treatment or prevention of alveolar destruction and/or the promotion of alveolar formation in a mammal. Such compositions comprise a ligand that is an RARβ antagonist or inverse agonist. In a preferred aspect of this embodiment, the RARβ receptor antagonist or inverse agonist has specific RAR modulating activity at the RARβ receptor, and is not specific to the RARα receptor. In another preferred aspect, the RARβ receptor antagonist or inverse agonist has specific RAR modulating activity at the RARβ receptor and is not specific to the RARγ receptor. In a particularly preferred aspect of this embodiment, the RARβ receptor antagonist or inverse agonist has specific RAR modulating activity at the RARβ receptor and is not specific to either the RARα or the RARγ receptor. Even more preferably, the ligand is specific to RARβ isotypes. Preferably such a ligand is a retinoid. Alveolar destruction may be the result of a pathological condition such as emphysema. Treatment to promote alveolar formation may be in response to a condition such as bronchopulmonary dysplasia (BPD).

Another aspect of the invention is methods for the treatment of treatment or prevention of alveolar destruction and/or the promotion of alveolar formation in a mammal, comprising administering a therapeutic amount of a composition comprising a retinoid receptor ligand that is an RARβ antagonist or inverse agonist. In a preferred aspect of this embodiment, the RARβ receptor antagonist or inverse agonist has specific RAR modulating activity at the RARβ receptor, and is not specific to the RARα receptor. In another preferred aspect, the RARβ receptor antagonist or inverse agonist has specific RAR modulating activity at the RARβ receptor and is not specific to the RARγ receptor. In a particularly preferred aspect of this embodiment, the RARβ receptor antagonist or inverse agonist has specific RAR modulating activity at the RARβ receptor and is not specific to either the RARα or the RARγ receptor. Even more preferably, the ligand is specific to RARβ isotypes. Preferably such a ligand is a retinoid.

The above-mentioned embodiments and aspects are clearly useful for the treatment of medical conditions, such as emphysema and BPD, which have been heretofore difficult or impossible to treat without a lung transplant. As indicated above, use of the RARβ antagonist or inverse agonist in combination with another agent with activity in treatment of alveolar deficiencies, such as all-trans-retinoic acid, is useful as well. Such methods and compositions may provide a synergistic therapeutic effect and/or permit the use of lower effective doses of ATRA or another therapeutic agent (and the RARβ antagonist or reverse agonist), thus reducing the prospect of undesired side effects resulting from the use higher concentrations of either agent when used alone.

The compositions of the present invention can be administered in any therapeutically effective manner or form, and in conjunction with any pharmacologically effective vehicle. For example, in a particularly preferred aspect, the compositions of the invention may be administered in the form of an inhalant as a powdered or liquid aerosol. Such a formulation may comprise the active agent solubilized in a micronized hydrophobic/hydrophilic emulsion. Such compositions are well known to those of skill in the art.

Alternatively, the compositions may be administered systemically, such as intravenously by infusion, or by intraperitoneal injection. For intravenous administration, the necessary composition of pharmacologically effective infusion solutions, such as the proper electrolyte balance and tonicity are well known to those of skill in the art, and therefore formulation of the compositions of the present invention with such solutions would be well within the ability of such a person with the disclosure of this application. Similarly, administration of drugs by intraperitoneal injection is well known, and pharmacological vehicles are well known.

Synthesis of candidate compounds having Specific RAR modulating activity is well-known in the art. For example, among other references, the synthesis of RAR ligands having antagonist and/or inverse agonist activity is disclosed in commonly owned U.S. Pat. Nos. 5,739,338; 5,728,846; 5,760,276; 5,877,207; the disclosures of all of which is incorporated by reference herein. Additionally, the construction of combinatorial libraries of compounds suitable for screening as RAR-selective ligands is now commonplace and well known to those of skill in the art.

Likewise, methods of screening candidate compounds for Specific RAR modulating activity is routine and well-known in the art. For example, U.S. Pat. No. 5,455,265, incorporated by reference herein, describes a chimeric receptor transactivation assay which tests for RAR-agonist activity in the RAR-α, RAR-β, RAR-γ, RXR-α receptor subtypes. Briefly, this assay employs chimeric proteins containing an RAR ligand-binding domain and a heterologous polypeptide segment having the ability to bind to a response element (RE), in turn facilitating transcription of a specific, measurable target gene, such as chloramphenicol acetyltransferase (CAT). Only an agonist of the given RAR isotype whose ligand binding domain comprises part of the chimeric protein will permit the activation of CAT transcription and expression. These results can be compared with those obtained using chimeric proteins having non-target ligand binding moieties. For example, those ligands able to stimulate CAT synthesis when used in combination with chimeric proteins having RAR binding domains, but not those having RXR ligand binding domains, will be RAR specific agonists.

Variation of this transactivation assay permits testing ligands as RAR antagonists, or antagonists of a given target isotype. A competitive assay involving the use of a stimulatory concentration of a known agonist of a given receptor (for example, ATRA is known to be an agonist of all RAR isotypes), and measuring the reduction in a reporter gene expression (e.g., CAT expression) as a function of the added candidate compound.

Additionally, straightforward receptor binding studies can be performed as competition, rather than transactivation assays. For example, and without limitation, membrane preparations containing cloned retinoid receptors can be used, and the receptors loaded with a known radiolabeled ligand. The release of radioactivity from these preparations as a function of test compound concentration can be determined. The lower the Kd for a given ligand, the more likely the ligand will be effective as a modulator of receptor activity. Further disclosure is available in, e.g., U.S. Pat. No. 5,776,699, previously incorporated by reference herein.

EXAMPLE 1

Involvement of RAR Receptors in Alveolus Formation

In most mammals new alveoli are formed postnatally; thus the lung of many newborn mammals is immature, and not merely a smaller version of the adult lung. For example, in humans alveolus formation can continue up to the age of 20.

The study of alveolus development in newborn mammals, in this case newborn rats, therefore provides an opportunity to study the effect of various agents on alveolus formation. The rate of increase in specific lung volume (expressed as $cm^3/100$ g body weight) in rats is greatest within the first 10 days following birth, after which it increases at a less steep rate.

However, the lung's efficiency is determined not merely by the volume of air that can be contained in the lung, but by the alveolar surface area, which is a function of tissue growth within the lung. Burri et al., *Anat. Rec.* 178:711–730 (1973) and Burri, Anat. Rec. 180: 77–98 (1974) performed extensive studies of the postnatal rat lung and demonstrated that three developmental phases can be shown. In the first stage (day 1–4) there is a massive expansion of the lung's volume. In the second stage, there is an increase in lung tissue proliferation due to septation, including alveolar and capillary surface areas. In the final stage (day 21 to adult) there is a period of concomitant tissue redistribution, lengthening of the septa and alveolar growth.

In this example, healthy 3-day old Sprague-Dawley rat pups were injected intraperitonally with either cottonseed oil (carrier) or with cottonseed oil containing 1 μl/gram of a retinoid ligand specific to RAR receptors and not to RXR receptors at a dosage of 500 micrograms per kg. This retinoid, termed AGN 193174, has RARβ agonist activity and the following structure:

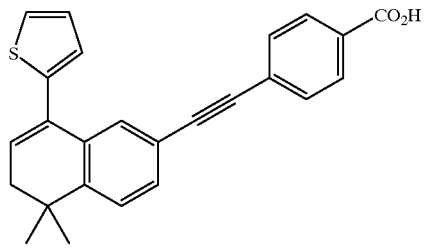

The expression of the RARβ receptor has been associated in certain cases with diminished cell replication. Following the initial injection, the rat pups were subjected to identical daily injections until day 13. A set of rat pups were sacrificed at day 4 and at day 21 by anesthesia with phenobarbitol sodium and scission of the abdominal aorta. Following sacrifice, rat lungs were fixed and histological sections prepared essentially as described in Massaro et al., *Am. J. Physiol.* 270: L305 (1996), incorporated by reference herein. The histological sections were viewed and photographs taken under light microscopy.

Figure 1B:
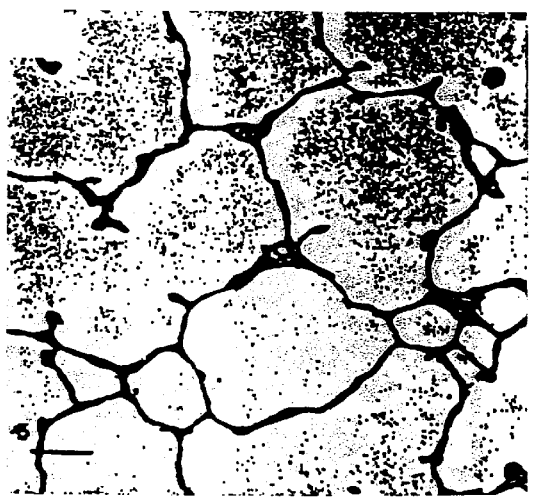
FIG. 1B is a photomicrograph of a histological section of the lung of a 14-day old rat injected intraperitoneally daily from age 3 to 13 days with an RARβ agonist dissolved in cottonseed oil.

The histological sections, replicated in FIGS. 1A and 1B, show that at age 14 days alveoli were larger, and the degree of sepatation less, in rats that had been treated with a RARβ agonist daily from age 3 through 13 days (the sepatation stage of lung development), than in rats treated with cottonseed oil alone.

The differences in alveolar dimensions between treated and untreated rat pups were so pronounced, they were quantitated by measuring the distance between alveolar walls (Lm) and the surface-to-volume ratio (S/V) of the gas-exchange structures (septa).

The Lm in cottonseed oil-treated rats was 80μm ±2.8 μm (N=4) compared to 110 μm ±7.3 μm (N=3) in RARβ agonist-treated rats (N=3; P=0.03 by Mann Whitney nonparametric analysis). The S/V was 504 μm$^{-1}$±μm$^1$ (N=4) in cottonseed oil-treated rats compared to 365 μm$^-$±23 μm$^{-1}$ (N=3) in RARβ agonist-treated rats (P=0.03). Lung volume was the same in both rat groups but surface area was larger (634 cm$^2$ ±9 cm$^2$) in cottonseed oil-treated rats than in RARβ agonist-treated rats (492 cm$^2$ ±28cm$^2$, P=0.03).

These data demonstrate that treatment of immature rats with a RARβ agonist inhibits septation of the saccules of the gas-exchange region, resulting in larger but fewer alveoli and a lower surface to volume ratio, and clearly suggest that agonist (positive) stimulation of the RARβ receptor results in the down-regulation of naturally occurring, spontaneous alveolus formation. A clear implication of this finding is the inverse is also true: that antagonist (neutralizing) or inverse agonist (negative) activity at the RARβ receptor is required for adequate sepation to occur. Thus, therapeutic treatment of mammals with an RAR antagonist or inverse agonist will promote the growth of septa.

It is quite surprising, in light of the previous finding that ATRA (an RAR-specific agonist of RARβ, RARα, and RARγ) stimulates septation, that a RARβ agonist is able to actually repress septation, and that therefore repression of signal transduction at RARβ through the action of an RARβ antagonist will promote septation.

EXAMPLE 2

Studies Mice lacking RARβ Receptors

This example employed a strain of mice that were uniformly lacking a functional gene for the RARβ receptor (RARβ knock-out or k.o. mice). As controls a founder strain of mice, identical to the RARβ k.o. mice but for the genetic lesion causing the lack of RARβ, were also examined. Animals from each group were sacrificed at 4 days and at 21 days, and histological sections of the lungs of animals from each group prepared and inspected as in Example 1. Photomicrographs are shown in FIGS. 2A–2D and additional results are shown below in Table 1.

TABLE 1

| Mice | n Sa cm$^2$ | Age Days | va × 10$^{-4}$ μm$^3$ | Na × 10$^{-6}$ | Na/kg × 10$^{-6}$ |
|---|---|---|---|---|---|
| Wild-type | 3 62 ± 2.7 | 4 | 17.6 ± 0.9 | 0.50 ± 0.03 | 193 ± 4.06 |
| RARβ k.o. | 3 65 ± 2.9 | 4 | 8.9 ± 0.6 | 0.95 ± 0.09 | 362 ± 16.0 |
| | P NS | | <0.05 | <0.05 | <0.05 |
| Wild-type | 4 215 ± 11.4 | 21 | 3.82 ± 0.15 | 5.35 ± 0.49 | 586 ± 38.3 |
| RARβ k.o. | 4 242 ± 9.6 | 21 | 2.38 ± 0.10 | 9.74 ± 0.05 | 918 ± 53.0 |
| | P NS | | 0.02 | 0.02 | 0.02 |

In Table 1, n is the number of animals sampled for each measurement, va is the mean volume of an individual alveolus, Na is the number of alveoli, and Sa is the alveolar surface area. Lung volume was measured by water displacement, va was measured by the point-sample intercepts method, and Sa was measured by point and intersection counting. Na was calculated.

Figure 2A:
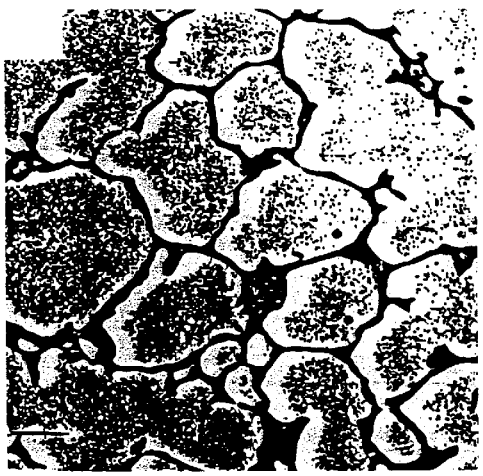
FIG. 2A is a photomicrograph of a histological section of the lung of a 4-day wild-type mouse.
Figure 2B:
FIG. 2B is a photomicrograph of a histological section of the lung of a 4-day mouse genetically lacking RARβ.
Figure 2C:
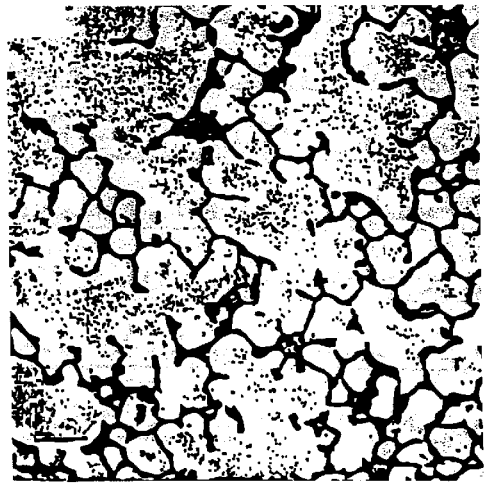
FIG. 2C is a photomicrograph of a histological section of the lung of a 21-day wild-type mouse.
Figure 2D:
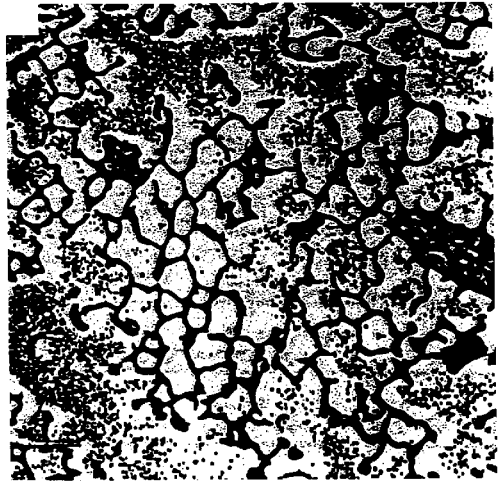
FIG. 2D is a photomicrograph of a histological section of the lung of a 21-day mouse genetically lacking RARβ.

The data show that lung volume did not differ between RARβ k.o. and wild-type mice at either age, but at both ages alveoli were smaller and more numerous in RARβ k.o. mice than in wild-type mice. These intergroup differences in alveolar dimensions were easily apparent in histological sections of lungs of 4-day old mice (FIGS. 2A and 2B) but less apparent in sections of lungs of 21-day old mice (FIGS. 2C and 2D). Alveolar surface area was not different between groups at 4 days, and slightly greater in the RARβ k.o. mice at day 14.

These data therefore provide strong evidence that alveolus formation is promoted in vivo by inhibition of the RARβ receptor. Negative regulation, as opposed to mere inhibition, of the same receptor may also be involved in alveolus formation.

The data also indicate that the increase in lung air volume seen in the first few days is an event independent from the presence or absence of RAR receptors or the presence or absence of an RAR modulating ligand, as shown in FIGS.

What is claimed is:

1. A compound having RARβ antagonist activity comprising the structural formula:

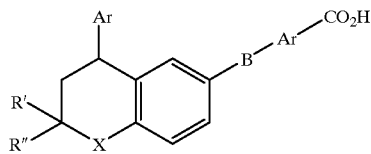

wherein
a) X is selected from the group consisting of $CR_2$;
b) R, R' and R" are each independently selected from the group consisting of H and lower alkyl;
c) Ar and Ar' are each independently a single ring aryl moiety; and
d) B is selected from the group consisting of —CR'CH—, —CHCR'—, —COO—, —OOC—; —COHN—; —NHOC—; —CSHN—; and —NHSC—.

2. The RARβ antagonist of claim 1 wherein Ar and Ar' are each independently selected from the group consisting of substituted or unsubstituted phenyl, furyl, thienyl and pyridyl groups.

3. A method of treating or preventing alveolar destruction in a mammal comprising the step of administering a therapeutically effective amount of an RARβ antagonist having specific RAR modulating activity to said mammal, wherein said RARβ antagonist has a structural formula:

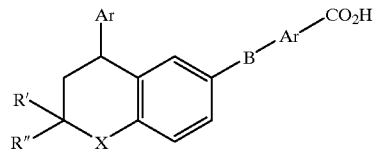

wherein
a) X is selected from the group consisting of $CR_2$;
b) $R_1$, R' and R" are each independently selected from the group consisting of H and lower alkyl;
c) Ar and Ar' are each independently a single ring aryl moiety; and
d) B is selected from the group consisting of —CR'CH—, —CHCR'—, —COO—, —OOC—; —COHN—; —NHOC—; —CSHN—; and —NHSC—.

4. The method of claim 3, wherein said RARβ antagonist is not specific to RARα.

5. The method of claim 3 wherein said RARβ antagonist is not specific to RARγ.

6. The method of claim 3 wherein said RARβ antagonist is not specific to RARα or RARγ.

7. The method of claim 3, wherein said composition is administered in the form of an inhalant.

* * * * *

UNITED STATES PATENT AND TRADEMARK OFFICE
CERTIFICATE OF CORRECTION

PATENT NO. : 6,303,648 B1
DATED : October 16, 2001
INVENTOR(S) : Massaro et al

It is certified that error appears in the above-identified patent and that said Letters Patent is hereby corrected as shown below:

Column 3,
Line 39, delete "RAR$\beta$" and insert in place thereof -- RAR$\gamma$ --
Line 50, delete "retinoido" and insert in place thereof -- retinoid --

Column 7,
Line 53, delete "$\mu m^1$" and insert in place thereof -- $18\mu m^{-1}$ --

Signed and Sealed this

Twelfth Day of March, 2002

Attest:

JAMES E. ROGAN
Attesting Officer          Director of the United States Patent and Trademark Office